(12) United States Patent
Candau

(10) Patent No.: US 6,214,323 B1
(45) Date of Patent: Apr. 10, 2001

(54) PHOTOPROTECTIVE/COSMETIC COMPOSITIONS COMPRISING CAMPHORSULFONIC ACID, BISRESORCINYLTRIAZINE AND BENZOAZOLYL/BENZODIAZOLYL SUNSCREENS

(75) Inventor: Didier Candau, Bievres (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/503,169

(22) Filed: Feb. 14, 2000

(30) Foreign Application Priority Data

Feb. 12, 1999 (FR) .................................................. 99 01733

(51) Int. Cl.⁷ ................................ A61K 7/42; A61K 7/44; A61K 7/00
(52) U.S. Cl. .............................. 424/59; 424/60; 424/400; 424/401
(58) Field of Search ................................ 424/59, 60, 400, 424/401

(56) References Cited

FOREIGN PATENT DOCUMENTS

| 196 45 317 A1 | 5/1998 | (DE) . |
| 0 669 323 A1 | 8/1995 | (EP) . |
| WO 98/22447 | 8/1998 | (WO) . |
| WO 99/08653 | 2/1999 | (WO) . |

*Primary Examiner*—Shelley A. Dodson
(74) *Attorney, Agent, or Firm*—Burns, Doane, Swecker & Mathis, L.L.P.

(57) ABSTRACT

Topically applicable sunscreen/cosmetic compositions well suited for the synergistically enhanced photoprotection of human skin and/or hair against the damaging effects of UV-irradiation, particularly solar radiation, comprise synergistically UV-photoprotecting effective amounts of each of (a) benzene-1,4-bis(3-methylidene-10-camphorsulfonic acid), optionally in neutralized form thereof, (b) at least one bisresorcinyltriazine compound, and (c) at least one compound containing at least two benzoazolyl groups or at least one benzodiazolyl group, formulated into a topically applicable, cosmetically acceptable vehicle, diluent or carrier therefor.

34 Claims, No Drawings

PHOTOPROTECTIVE/COSMETIC COMPOSITIONS COMPRISING CAMPHORSULFONIC ACID, BISRESORCINYLTRIAZINE AND BENZOAZOLYL/BENZODIAZOLYL SUNSCREENS

CROSS-REFERENCE TO PRIORITY APPLICATION

This application claims priority under 35 U.S.C. §119 of FR-99/01733, filed Feb. 12, 1999, hereby expressly incorporated by reference.

CROSS-REFERENCE TO COMPANION APPLICATIONS

Copending applications Ser. No. 09/503,943, Ser. No. 09/503,944, Ser. No. 09/503,941, and Ser. No. 09/503,940, each filed concurrently herewith and each assigned to the assignee hereof.

BACKGROUND OF THE INVENTION

1. Technical Field of the Invention

The present invention relates to novel cosmetic compositions for topical application, for photoprotecting the skin and/or the hair against ultraviolet radiation (such compositions hereinafter simply designated "antisun," "sunscreen" or "photoprotective" compositions), and to the use of same for the cosmetic applications indicated above.

This invention more especially relates to the aforesaid sunscreen/cosmetic compositions comprising, formulated into a cosmetically acceptable vehicle, diluent or carrier therefor, a tripartite combination of (a) benzene-1,4-bis(3-methylidene-10-camphorsulfonic acid), optionally in partially or totally neutralized form, as a first screening agent, (b) at least one bisresorcinyltriazine compound as a second screening agent, and (c) as a third screening agent, at least one compound containing at least two benzoazolyl groups or a compound containing at least one benzodiazolyl group, the said first, second and third screening agents being present in the subject compositions in proportions suitable for eliciting a synergistic effect with regard to the protection factors imparted.

2. Description of the Prior Art

It is known to this art that light radiation of wavelengths of from 280 nm to 400 nm promotes tanning of the human epidermis and that irradiation with wavelengths of from 280 to 320 nm, i.e., UV-B radiation, causes skin burns and erythema which may be harmful to the development of a natural tan; this UV-B radiation should thus be screened from the skin.

It is also known to this art that UV-A radiation, with wavelengths of from 320 to 400 nm, which causes tanning of the skin, also adversely affects it, in particular in the case of sensitive skin or of skin which is continually exposed to solar radiation. UV-A rays in particular cause a loss of skin elasticity and the appearance of wrinkles, resulting in premature aging. Such irradiation promotes triggering of the erythemal reaction or amplifies this reaction in certain individuals and may even be the cause of phototoxic or photoallergic reactions. It is thus desirable to also screen out UV-A radiation.

A wide variety of cosmetic compositions for photoprotecting (against UV-A and/or UV-B) the skin are known to this art.

These photoprotective/sunscreen compositions are typically emulsions of oil-in-water type (i.e., a cosmetically acceptable support (vehicle, diluent or carrier) comprising an aqueous dispersing continuous phase and an oily dispersed discontinuous phase) which contains, in various concentrations, one or more conventional lipophilic and/or hydrophilic organic screening agents capable of selectively absorbing harmful UV radiation, these screening agents (and the amounts thereof) being selected as a function of the desired protection factor (the protection factor (PF) being expressed mathematically by the ratio of the irradiation time required to attain the erythema-forming threshold with the UV screening agent to the time required to attain the erythema-forming threshold without a UV screening agent).

SUMMARY OF THE INVENTION

It has now surprisingly and unexpectedly been determined that a tripartite combination of three specific sunscreens already per se known to this art provides synergistically active sunscreen compositions exhibiting markedly improved protection factors.

Briefly, the present invention features novel cosmetic compositions, in particular photoprotective/sunscreen compositions, comprising, in a cosmetically acceptable vehicle, diluent or carrier, (a) benzene-1,4-bis(3-methylidene-10-camphorsulfonic acid), optionally in partially or totally neutralized form, as a first screening agent, (b) at least one bisresorcinyltriazine compound as a second screening agent, and (c) as a third screening agent, at least one compound containing at least two benzoazolyl groups or a compound containing at least one benzodiazolyl group, the said first, second and third screening agents being formulated into the subject compositions in proportions which elicit a synergistic effect with regard to the protection factors imparted.

The present invention also features the use of the subject compositions for the production of cosmetic compositions suited for photoprotecting the skin and/or the hair against the deleterious effects of ultraviolet radiation, in particular solar radiation.

This invention thus also features a cosmetic regime/regimen for photoprotecting the skin and/or the hair against the damaging effect of ultraviolet radiation, in particular solar radiation, which essentially entails topically applying onto the skin/hair an effective photoprotecting amount of a composition in accordance herewith.

DETAILED DESCRIPTION OF BEST MODE AND SPECIFIC/PREFERRED EMBODIMENTS OF THE INVENTION

More particularly according to the present invention, novel cosmetic or dermatological compositions, in particular sunscreen/antisun compositions, are now provided, comprising, formulated into vehicle, diluent or carrier therefor:

(a) benzene-1,4-bis(3-methylidene-10-camphorsulfonic acid), optionally in partially or totally neutralized form, as a first screening agent;

(b) as a second screening agent, at least one bisresorcinyltriazine compound;

(c) as a third screening agent, at least one compound containing at least two benzoazolyl groups per molecule and/or at least one compound containing, per molecule, at least one benzodiazolyl group, the said first, second and third screening agents being formulated into the subject compositions in proportions which elicit a synergistic effect with regard to the sun protection factors imparted.

By the expression "containing at least two benzazolyl groups" are intended, per molecule, at least two groups of the benzoxazolyl, benzothiazolyl or benzimidazolyl type.

By the expression "containing at least one benzodiazolyl group" is intended, per molecule, one group of the benzodioxazolyl, benzodithiazolyl or benzodiimidazolyl type.

Benzene-1,4-bis(3-methylidene-10-camphorsulfonic acid) and the various salts thereof, described, in particular, in FR-A-2,528,420 and FR-A-2,639,347, are screening agents that are already known per se (so-called broad-band screening agents) which are capable of absorbing ultraviolet radiation with wavelengths of from 280 to 400 nm, with absorption maxima of from 320 to 400 nm, in particular at about 345 nm.

These screening agents have the structural formula (I) below:

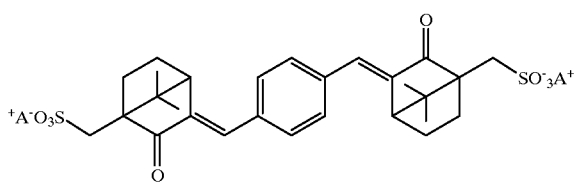

(I)

in which A is a hydrogen atom, an alkali metal or a radical $NH(R)_3^+$ in which the radicals R, which may be identical or different, are each a hydrogen atom, a $C_1$–$C_4$ alkyl or hydroxyalkyl radical, or a group $M^{n+}/n$, wherein $M^+$ is a multivalent metal cation in which n is equal to 2, 3 or 4, $M^+$ preferably being a metal cation selected from among $Ca^{2+}$, $Zn^{2+}$, $Mg^{2+}$, $Ba^{2+}$, $Al^{3+}$ and $Zr^{4+}$. It will be appreciated that the compounds of formula (I) above also comprehend the "cis-trans" isomer about one or more double bond(s) and that all such isomers are within the scope of the present invention.

The benzene-1,4-bis(3-methylidene-10-camphorsulfonic acid), and/or one of the various salts thereof, is advantageously present in the screening compositions according to the invention in a total concentration ranging from 0.1% to 15% by weight, approximately, and preferably from 0.2% to 10% by weight, approximately, relative to the total weight of the composition.

The bisresorcinyltriazine compounds according to the present invention are preferably selected from among those having the structural formula (II) below:

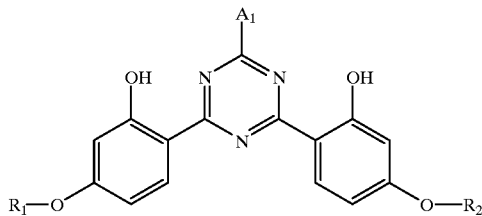

(II)

in which (i) the radicals $R_1$ and $R_2$, which may be identical or different, are each a $C_3$–$C_{18}$ alkyl radical, a $C_2$–$C_{18}$ alkenyl radical, or a residue of formula —$CH_2$—$CH(OH)$—$CH_2$—$OT_1$ in which $T_1$ is a hydrogen atom or a $C_1$–$C_8$ alkyl radical; or (ii) the radicals $R_1$ and $R_2$, which again may be identical or different, are also each a residue of formula (1) below:

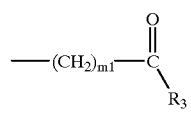

(1)

in which $m_1$ is a number ranging from 1 to 3; $R_3$ is a hydroxyl group, a $C_1$–$C_5$ alkyl radical which is unsubstituted or substituted with one or more hydroxyl groups, a $C_1$–$C_5$ alkoxy radical, an amino group, a mono- or di($C_1$–$C_5$)alkylamino radical, a metal cation M, a residue having one of the formulae (2) to (7) below:

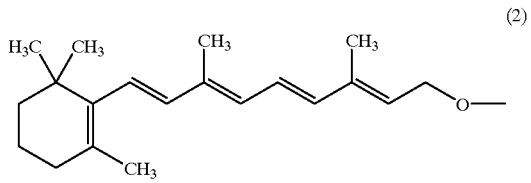

(2)

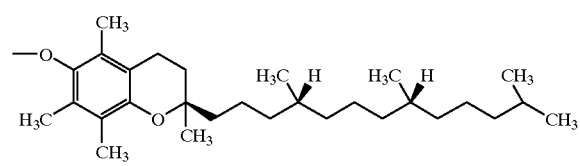

(3)

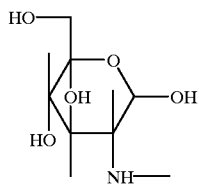

(4)

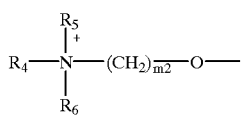

(5)

-continued (6)

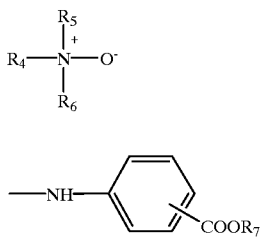

(7)

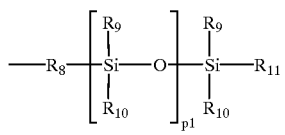

in which the radicals $R_4$, $R_5$ and $R_6$, which may be identical or different, are each a $C_1$–$C_1$–$C_{14}$ alkyl radical which is unsubstituted or substituted with one or more hydroxyl groups; $R_7$ is a hydrogen atom, a metal cation M, a $C_1$–$C_5$ alkyl radical, or a residue of formula —$(CH_2)_{m2}$—$OT_1$ in which $m_2$ is a number ranging from 1 to 4 and $T_1$ is as defined above; or (iii) the radicals $R_1$ and $R_2$, which again may be identical or different, are also each a residue of formula (8) below:

(8)

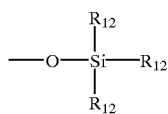

in which $R_8$ is a covalent bond, a linear or branched $C_1$–$C_4$ alkyl radical, or a residue of formula —$C_{m4}H_{2m4}$— or —$C_{m4}H_{2m4}$—O— in which $m_4$ is a number ranging from 1 to 4; $p_1$ is a number ranging from 0 to 5; the radicals $R_9$, $R_{10}$ and $R_{11}$, which may be identical or different, are each a $C_1$–$C_{18}$ alkyl radical, a $C_1$–$C_{18}$ alkoxy radical, or a residue of the formula:

(9)

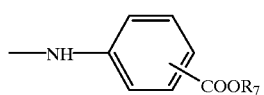

in which $R_{12}$ is a $C_1$–$C_5$ alkyl radical; $A_1$ is a residue have one of the following formulae:

(7)

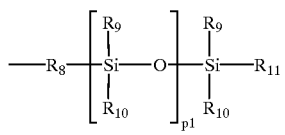

(10)

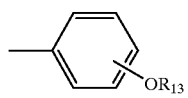

(11)

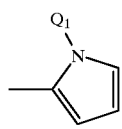

(12)

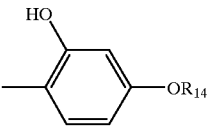

in which $R_7$ is as defined above: $R_{13}$ is a hydrogen atom, a $C_1$–$C_{10}$ alkyl radical, a radical of formula: $(CH_2CHR_{16}$—O$)_{n1}R_7$ in which $n_1$ is a number ranging from 1 to 16, $R_{16}$ is a hydrogen atom or methyl, or a residue of structure —$CH_2$—CH—(OH)—$CH_2OT_1$ wherein $T_1$ is as defined above; $Q_1$ is a $C_1$–$C_{18}$ alkyl radical; —$R_{14}$ is a radical having the formula (1):

(1)

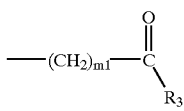

as defined above.

In the above formulae (II) and (1) to (12):

the alkyl radicals are advantageously linear or branched and selected, for example, from among methyl, ethyl, n-propyl, isopropyl, n-butyl, sec-butyl, tert-butyl, amyl, isoamyl, tert-amyl, heptyl, octyl, isooctyl, nonyl, decyl, undecyl, dodecyl, tetradecyl, pentadecyl, hexadecyl, heptadecyl and octadecyl;

the alkenyl radicals can be chosen, for example, from allyl, methallyl, isopropenyl, 2-butenyl, 3-butenyl, isobutenyl, n-penta-2,4-dienyl, 3-methyl-2-butenyl, n-oct-2-enyl, n-dodec-2-enyl, isododecenyl and n-octadec-4-enyl;

the alkoxy radicals are linear or branched and are advantageously selected, for example, from among methoxy, ethoxy, n-propoxy, isopropoxy, n-butoxy, sec-butoxy, tert-butoxy, amyloxy, isoamyloxy and tert-amyloxy;

the $C_1$–$C_5$ mono- or dialkylamino radicals can be chosen, for example, from methylamino, ethylamino, propylamino, n-butylamino, sec-butylamino, tert-butylamino, pentylamino, dimethylamino, diethylamino, dibutylamino and methylethylamino;

the metal cations are alkali metal, alkaline-earth metal or metal cations selected, for example, from among lithium, potassium, sodium, calcium, magnesium, copper and zinc.

The bisresorcinyltriazine compounds of formula (II) of the invention are screening agents that are already per se known. They are described and prepared according to the syntheses illustrated in EP-A-0,775,698 and EP-A-0,878,469, hereby expressly incorporated by reference.

Exemplary bisresorcinyltriazine compounds of formula (II) are those in which the radical $A_1$ is para-methoxyphenyl or para-ethoxyphenyl and the radicals $R_1$ and $R_2$, which may be identical or different, are each a radical of the formula:

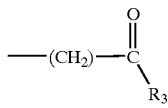

in which R₃ is:
tert-butyloxy;
OH;
OM in which M is an alkali metal, or alkaline-earth metal cation selected from among copper, magnesium or zinc;
a group of the structure:

a group of the structure O⁻N⁺(CH₂CH₂OH)₃;
a group of the structure:

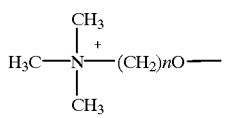

wherein n ranged from 2 to 16;
a group of the structure:

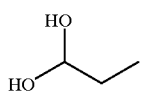

or a group of the structure:

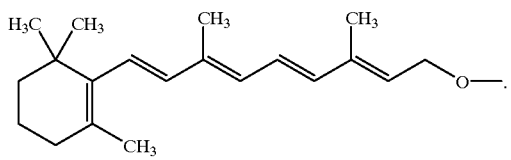

Also exemplary of the bisresorcinyltriazine compounds having the formula (II) is that in which the radical A₁ is para-hydroxyphenyl and the radicals R₁ and R₂ simultaneously are each a group of the formula:

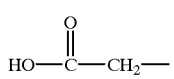

Particularly exemplary compounds of formula (II) include:
2,4-bis{[4-(2-ethylhexyloxy)-2-hydroxy]phenyl}-6-(4-methoxyphenyl)-1,3,5-triazine;
2,4-bis{[4-3-(2-propyloxy)-2-hydroxypropyloxy]-2-hydroxy]phenyl}-6-(4-methoxyphenyl)-1,3,5-triazine;
2,4-bis{[4-(2-ethylhexyloxy)-2-hydroxy]phenyl}-6-[4-(2-methoxyethylcarboxyl)phenylamino]-1,3,5-triazine;
2,4-bis{[4-tris(trimethylsiloxysilylpropyloxy)-2-hydroxy]phenyl}-6-(4-methoxyphenyl)-1,3,5-triazine;
2,4-bis{[4-(2"-methylpropenyloxy)-2-hydroxy]phenyl}-6-(4-methoxyphenyl)-1,3,5-triazine;
2,4-bis{[4-(1',1',1',3',5',5',5'-heptamethyl-trisiloxy-2"-methylpropyloxy)-2-hydroxy]phenyl}-6-(4-methoxyphenyl)-1,3,5-triazine;
2,4-bis{[4-(3-(2-propyloxy)-2-hydroxypropyloxy]2-hydroxy]phenyl}-6-[(4-ethylcarboxyl)phenylamino]-1,3,5-triazine;
2,4-bis{[4-(2-ethylhexyloxy)-2-hydroxy]phenyl}-6-(1-methyl-2-pyrrolyl)-1,3,5-triazine.

The bisresorcinyltriazine compounds of formula (II) which are more particularly preferred according to the invention are selected from the group consisting of:
2,4-bis{[4-(2-ethylhexyloxy)-2-hydroxy]phenyl}-6-(4-methoxyphenyl)-1,3,5-triazine;
2,4-bis{[4-tris(trimethylsiloxysilylpropyloxy)-2-hydroxy]phenyl}-6-(4-methoxyphenyl)-1,3,5-triazine;
2,4-bis{[4-(1',1',1',3',5',5',5'-heptamethyl-trisiloxy-2"-methylpropyloxy)-2-hydroxy]phenyl}-6-(4-methoxyphenyl)-1,3,5-triazine.

The organic screening agent(s) of the bisresorcinyltriazine compound type are advantageously present in the screening compositions according to the invention in a total concentration ranging from 0.1% to 15% by weight, approximately, and preferably from 0.2% to 10% by weight, approximately, relative to the total weight of the composition.

Exemplary compounds containing at least two benzoazolyl groups in accordance with the invention are preferably those having the structural formula (III) below:

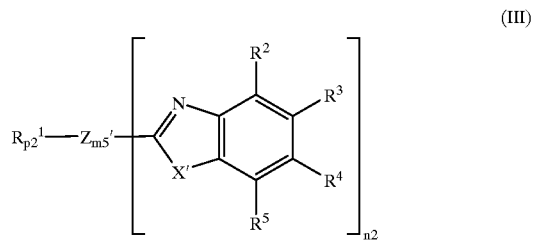

in which Z' is an organic residue of valency ($p_2+n_2$) comprising one or more double bonds situated such that it completes the system of double bonds of at least two benzoazolyl groups as defined in the brackets, to form a totally conjugated assembly; X' is S, O or NR⁶; R¹ is a hydrogen atom, $C_1–C_{18}$ alkyl radical, $C_1–C_4$ alkoxy radical, a $C_5–C_{15}$ aryl radical, a $C_2–C_{18}$ acyloxy radical, SO₃Y' or COOY'; the radicals R², R³, R⁴ and R⁵, which may be identical or different, are each a nitro group, or a radical R¹; R⁶ is a hydrogen atom, a $C_1–C_4$ alkyl radical, or a $C_1–C_4$ hydroxyalkyl radical; Y' is a hydrogen atom, Li, Na, K, NH₄, ½Ca, ½Mg, ⅓Al, or a cation resulting from the neutralization of a free acid group with an organic nitrogenous base; $m_5$ is 0 or 1; $n_2$ is a number ranging from 2 to 6; $p_2$ is a number ranging from 1 to 4; with the proviso that $p_2+n_2$ does not exceed 6.

The compounds of formula (III) according to the invention are water-soluble UV-A screening agents that are already known and described in EP-A-0 669 323. They are also described and prepared according to the syntheses indicated in U.S. Pat. No. 2,463,264 and in EP-A-0 669 323, hereby expressly incorporated by reference.

Among the compounds of formula (III) of the invention, preferred are those in which the radical Z' is selected from among:

(a) a linear olefinic aliphatic $C_2$–$C_6$ hydrocarbon-based radical which may be interrupted with a $C_5$–$C_{12}$ aryl radical or a $C_4$–$C_{12}$ heteroaryl radical, such as, for example:

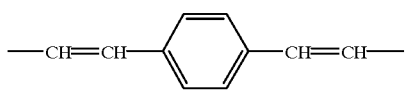

(b) a $C_5$–$C_{15}$ aryl radical which may be interrupted with a linear olefinic aliphatic $C_2$–$C_6$ hydrocarbon-based radical such as, for example, the following:

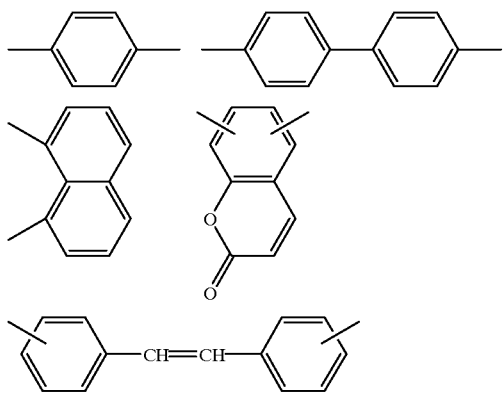

(c) a $C_3$–$C_{10}$ heteroaryl radical such as, for example, the following:

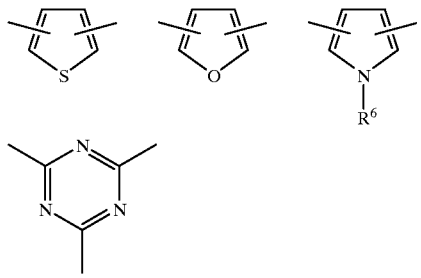

in which $R^6$ is as defined above; with the proviso that the said radicals Z' as defined in paragraphs (a), (b) and (c) may be substituted with $C_1$–$C_6$ alkyl, $C_1$–$C_6$ alkoxy, phenoxy, hydroxyl, methylenedioxy or amino radicals optionally substituted with one or two $C_1$–$C_5$ alkyl radicals.

Exemplary compounds of formula (III) are the following, as well as the salts thereof:

Compound 1

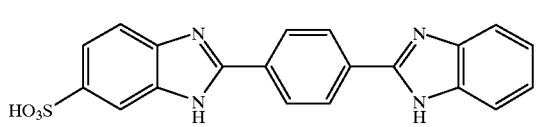

Compound 2

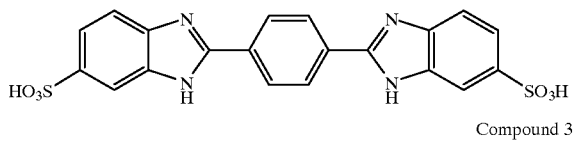

Compound 3

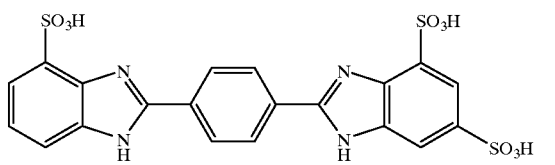

Compound 4

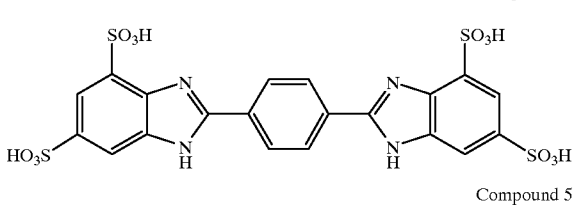

Compound 5

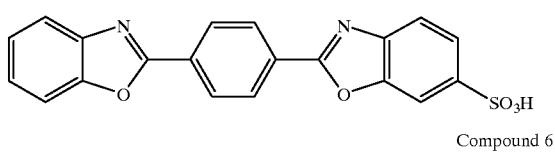

Compound 6

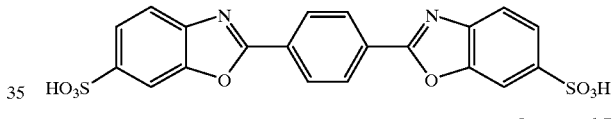

Compound 7

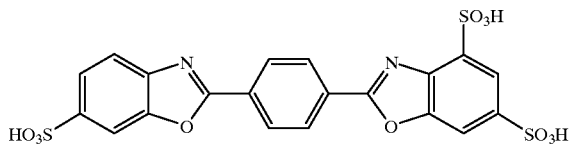

Compound 8

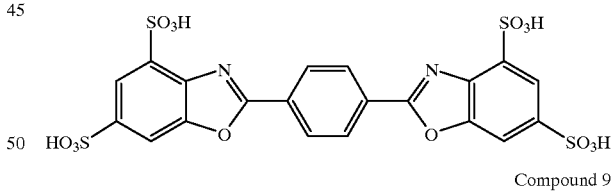

Compound 9

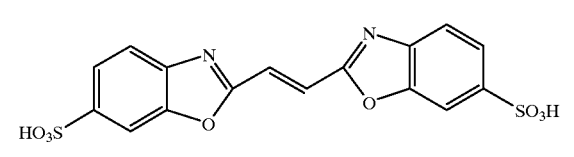

Compound 10

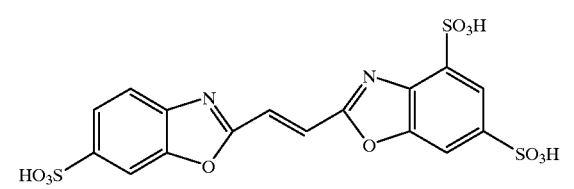

Compound 11
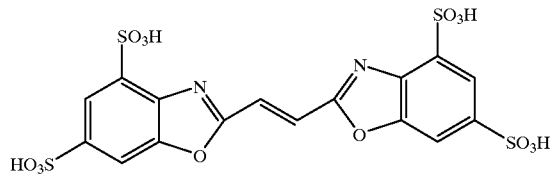
Compound 12
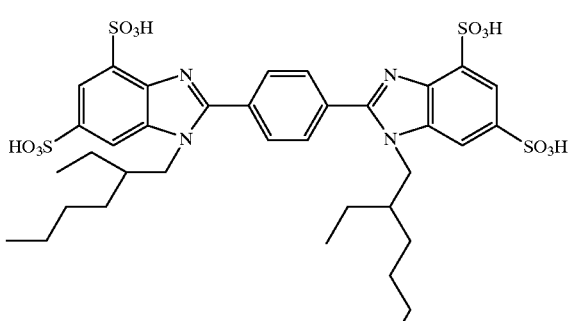
Compound 13
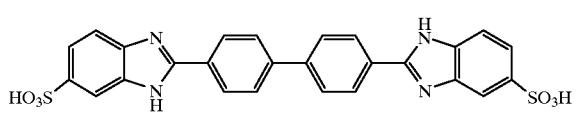
Compound 14
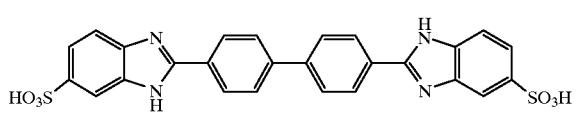
Compound 15
Compound 16
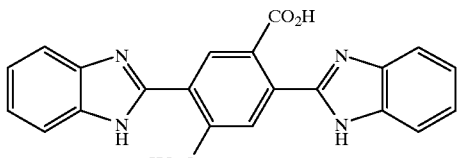
Compound 17
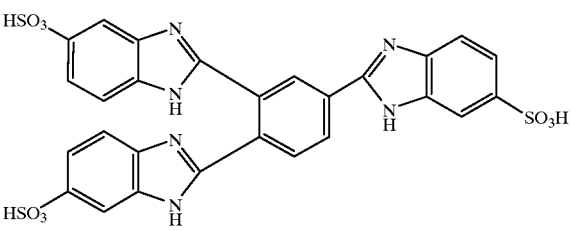
Compound 18
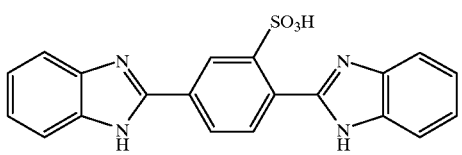
Compound 19
Compound 20
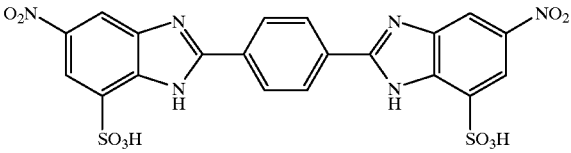
Compound 21
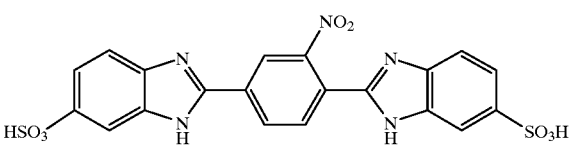
Compound 22
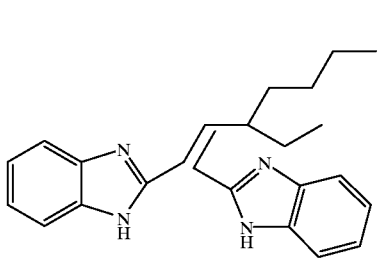

-continued

Compound 23

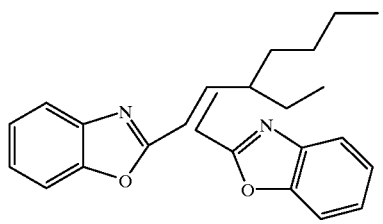

Compound 24

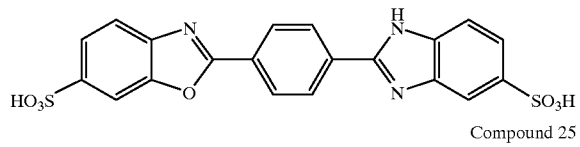

Compound 25

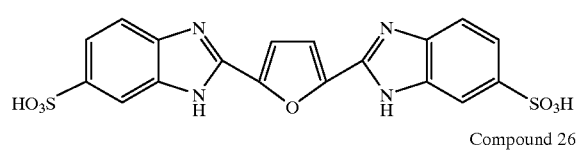

Compound 26

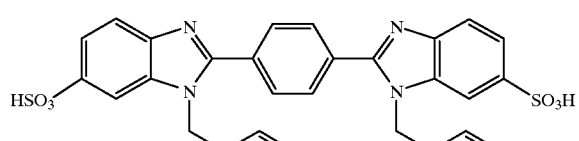

Compound 27

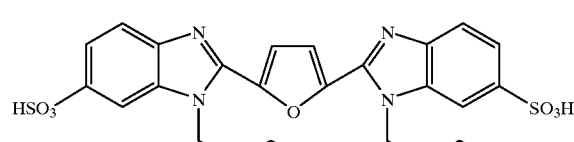

Among these compounds, the most particularly preferred is 1,4-bis(benzimidazolyl)phenylene-3,3',5,5'-tetrasulfonic acid (Compound 4), as well as the salts thereof, having the following structural formula:

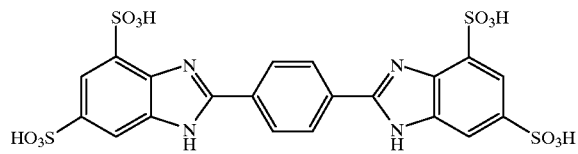

Also exemplary of the compounds containing at least two benzoazolyl groups are the following compounds, as well as the salts thereof:

Compound 28

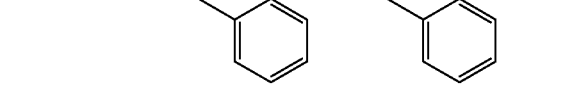

Compound 29

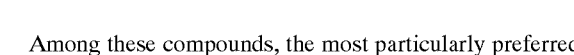

Compound 30

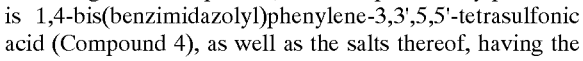

Compound 31

Exemplary compounds containing at least one benzodiazolyl group according to the invention are the following, as well as the addition salts thereof:

Compound 32

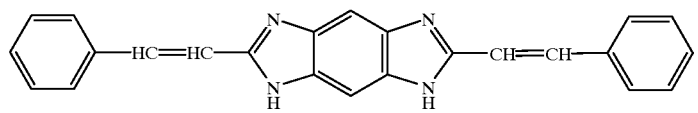

Compound 33

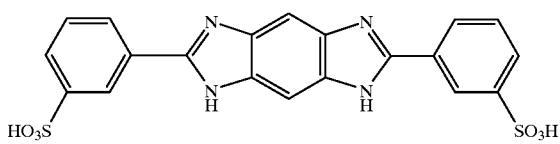

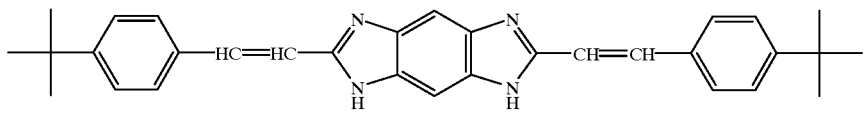

Compound 34

The compound(s) containing benzoazolyl or benzodiazolyl groups in accordance with the invention are advantageously present in the compositions according to the invention in a concentration ranging from 0.1% to 15%, preferably from 0.2% to 10% by weight relative to the total weight of the composition.

As indicated above, in a characteristic embodiment of the present invention, the subject three types of sunscreens are each present in the final composition in respective proportions such that a substantial and significant synergistic effect is obtained with regard to the protection factor imparted by the resulting combination.

In addition, and generally, it should be noted that the concentrations and ratios of the benzene-1,4-bis(3-methylidene-10-camphorsulfonic acid), of the bisresorcinyl-triazine compound and of the compound containing benzoazolyl or benzodiazolyl groups as defined above are selected such that the sun protection factor of the final composition is preferably at least 2.

In another preferred embodiment of the present invention, the cosmetically acceptable support (vehicle, diluent or carrier) in which the various screening agents are formulated is an emulsion of oil-in-water type.

The sunscreen/antisun cosmetic compositions according to the invention can contain one or more additional hydrophilic or lipophilic sunscreens that are active in the UV-A and/or UV-B range (absorbers), other than, of course, the three screening agents indicated above. These additional screening agents are advantageously selected, in particular, from among cinnamic derivatives; salicylic derivatives; camphor derivatives; triazine derivatives other than those defined above, such as those described in EP-863,145, EP-517,104, EP-570,838 and EP-796,851; benzophenone derivatives; dibenzoylmethane derivatives; β,β'-diphenylacrylate derivatives, and benzimidazole derivatives other than those described above; p-aminobenzoic acid derivatives; screening polymers and screening silicones, such as those described in WO- 93/04665.

Exemplary such additional sunscreens that are active in the UV-A and/or UV-B range include:
p-aminobenzoic acid;
oxyethylenated (25 mol) p-aminobenzoate;
-ethylhexyl p-dimethylaminobenzoate;
N-oxypropylenated ethyl p-aminobenzoate;
glyceryl p-aminobenzoate;
homomenthyl salicylate;
2-ethylhexyl salicylate;
triethanolamine salicylate;
4-isopropylbenzyl salicylate;
4-tert-butyl-4'-methoxydibenzoylmethane;
4-isopropyldibenzoylmethane;
2-ethylhexyl 4-methoxycinnamate;
methyl diisopropylcinnamate;
isoamyl 4-methoxycinnamate;
diethanolamine 4-methoxycinnamate;
menthyl anthranilate;
2-ethylhexyl-2-cyano-3,3'-diphenylacrylate;
ethyl-2-cyano-3,3'-diphenylacrylate;
2-phenylbenzimidazole-5-sulfonic acid and its salts;
3-(4'-trimethylanmmonio)benzylidene-2-bornanone methyl sulfate;
2-hydroxy-4-methoxybenzophenone;
2-hydroxy-4-methoxybenzophenone 5-sulfonate;
2,4-dihydroxybenzophenone;
2,2',4,4'-tetrahydroxybenzophenone;
2,2'-dihydroxy-4,4,-dimethoxybenzophenone;
2-hydroxy-4-n-octoxybenzophenone;
2-hydroxy-4-methoxy-4'-methylbenzophenone;
urocanic acid;
α-(2-oxo-3-bornylidene)-4-toluenesulfonic acid and its salts;
-(4'-sulfo)benzylidene-2-bornanone and its salts;
3-(4'-methylbenzylidene)-d,l-camphor;
3-benzylidene-d,l-camphor;
2,4,6-tris[p-(2'-ethylhexyl-1'-oxycarbonyl)anilino]-1,3,5-triazine;
2-[p-(tert-butylamido)anilino]-4,6-bis[(p-(2'-ethyl- hexyl-1'-oxycarbonyl)anilino]-1,3,5-triazine;
N-(2 and 4)-{[(2-oxo-3-bornylidene)methyl]-benzyl}acrylamide polymer;
drometrizole trisiloxane (INCI designation);
polyorganosiloxanes containing a malonate function.

The compositions according to the invention can also contain active agents for artificially tanning and/or browning the skin (self-tanning agents), such as, for example, dihydroxyacetone (DHA).

The cosmetic compositions according to the invention can also contain pigments or nanopigments (average size of the primary particles: generally ranging from 5 nm to 100 nm, preferably between 10 nm and 50 nm) of coated or uncoated metal oxides, such as, for example, nanopigments of titanium dioxide (amorphous or crystallized in rutile and/or anatase form), of iron oxide, of zinc oxide, of zirconium oxide or of cerium oxide, which are all UV photoprotective agents that are well known per se. Conventional coating agents are, moreover, alumina and/or aluminum stearate. Such coated or uncoated metal oxide nanopigments are described, in particular, in EP-A-0,518,772 and EP-A-0,518,773.

The compositions of the invention can also contain conventional cosmetic additives and adjuvants selected, in particular, from among fatty substances, organic solvents, thickeners, softeners, antioxidants, opacifiers, stabilizers, emollients, hydroxy acids, antifoaming agents, moisturizers, vitamins, fragrances, preserving agents, surfactants, fillers, sequestering agents, propellants, acidifying or basifying agents, dyes, colorants, or any other ingredient usually used in cosmetics, in particular for the production of antisun/sunscreen compositions formulated as emulsions.

Exemplary fatty substances include oils or waxes or mixtures thereof, and they also comprise fatty acids, fatty alcohols and fatty acid esters. The oils are selected from among animal, plant, mineral or synthetic oils and in particular from liquid petroleum jelly, liquid paraffin, volatile or non-volatile silicone oils, isoparaffins, poly-α-olefins, fluoro oils and perfluoro oils. Similarly, the waxes are advantageously selected from among the animal, fossil, plant, mineral and synthetic waxes which are per se even known to this art.

Exemplary organic solvents include the lower alcohols and polyols.

The thickeners are advantageously selected, in particular, from among crosslinked acrylic acid homopolymers, modified or unmodified guar gums and celluloses, such as hydroxypropyl guar gum, methylhydroxyethylcellulose, hydroxypropylmethylcellulose or hydroxyethylcellulose.

One skilled in this art will of course take care to select this or these optional additional compound(s) and/or the amounts thereof such that the advantageous properties, in particular the sun protection factors imparted, intrinsically provided by the ternary combination in accordance with the invention, are not, or are not substantially, adversely affected by the addition(s) envisaged.

The compositions of the invention are easily formulated according to the techniques well known to this art, in particular those suited for the formulation of emulsions of oil-in-water or water-in-oil type.

Such compositions can be provided, in particular, in the form of a simple or complex emulsion (O/W, W/O, O/W/O or W/O/W) such as a cream, a milk, a gel or a cream-gel, a lotion, an ointment, a powder or a solid tube or stick and can optionally be packaged as an aerosol and can be in the form of a mousse or a spray.

When formulated as an emulsion, the aqueous phase of this emulsion can comprise a nonionic vesicular dispersion prepared according to known techniques (Bangham, Standish and Watkins, *J. Mol. Biol.,* 13, 238 (1965), FR-2,315,991 and FR-2,416,008).

The cosmetic compositions of the invention are well suited for protecting the human epidermis or the hair against ultraviolet rays, as an antisun/sunscreen composition or as a makeup product.

When the cosmetic compositions according to the invention are used for photoprotecting the human epidermis against UV irradiation or as sunscreen/antisun compositions, they can be provided in the form of a suspension or dispersion in solvents or fatty substances, in the form of a nonionic vesicular dispersion, or in the form of an emulsion, preferably of oil-in-water type, such as a cream or a milk, in the form of an ointment, a gel, a cream-gel, a solid tube, a stick, an aerosol mousse or a spray.

When the cosmetic composition according to the invention are used for photoprotecting the hair, they can be provided in the form of a shampoo, a lotion, a gel, an emulsion or a nonionic vesicular dispersion and can constitute, for example, a rinse-out composition, to be applied before or after shampooing, before or after dyeing or bleaching, before, during or after permanent-waving or straightening the hair, a styling or treating lotion or gel, a blow-drying or hairsetting lotion or gel, or a permanent-waving, straightening, dyeing or bleaching composition for the hair.

When the subject compositions are used as a makeup product for the eyelashes, the eyebrows or the skin, such as an epidermal treatment cream, a foundation, a tube of lipstick, an eyeshadow, a face powder, a mascara or an eyeliner, they can be in solid or pasty, anhydrous or aqueous form, such as oil-in-water or water-in-oil emulsions, nonionic vesicular dispersions or alternatively suspensions.

For example, for the antisun formulations in accordance with the invention which comprise a support of oil-in-water emulsion type, the aqueous phase (in particular comprising the hydrophilic screening agents) generally constitutes from 50% to 95% by weight, preferably from 70% to 90% by weight, relative to the total weight of the formulation, the oily phase (in particular comprising the lipophilic screening agents) generally constitutes from 5% to 50% by weight, preferably from 10% to 30% by weight, relative to the total weight of the formulation, and the (co)emulsifier(s) generally constitute(s) from 0.5% to 20% by weight, preferably from 2% to 10% by weight, relative to the total weight of the formulation.

As hereinbefore indicated, the present invention also features a regime/regimen for the cosmetic treatment of the skin or the hair deleteuous to protect these against the effects of UV radiation, comprising topically applying onto the skin or hair an effective photoprotecting amount of a subject cosmetic composition.

In order to further illustrate the present invention and the advantages thereof, the following specific examples are given, it being understood that same are intended only as illustrative and in nowise limitative.

In said example to follow, all parts and percentages are given by weight.

The following three (3) compositions according to the invention were formulated via conventional cosmetic technique.

EXAMPLE 1

| COMPOSITION | Example 1 |
| --- | --- |
| 80/20 mixture of cetylstearyl alcohol and of oxyethylenated (33 EO) cetylstearyl alcohol (Sinnowax AO - Henkel) | 7 g |
| Mixture of glyceryl monostearate and glyceryl distearate (Cerasynt SD-V - ISP) | 2 g |
| Cetyl alcohol | 1.5 g |
| Polydimethylsiloxane (Dow Corning 200 Fluid - Dow Corning) | 1 g |
| C12/C15 alkyl benzoates (Witconol TN - Witco) | 15 g |
| 2,4-bis{[4-(2-ethylhexyloxy)-2-hydroxy]phenyl}-6-(4-methoxyphenyl)-1,3,5-triazine | 2 g |
| Glycerol | 15 g |
| 1,4-Bis(benzimidazolyl)phenylene-3,3'5,5'-tetrasulfonic acid | 2 g |
| Benzene-1,4-bis(3-methylidene-10-camphorsulfonic acid) (Mexoryl SX - Chimex) | 2 g |
| Triethanolamine | qs pH 7 |
| Preservatives | qs |
| Demineralized water qs | 100 g |

EXAMPLE 2

| COMPOSITION | Example 2 |
|---|---|
| Glyceryl mono-/distearate/polyethylene glycol stearate (100 EO) mixture (Arlacel 165 FL - ICI) | 2 g |
| Stearyl alcohol (Lanette 18 - Henkel) | 1 g |
| Stearic acid from palm oil (Stearine TP - Stearinerie Dubois) | 2.5 g |
| Polydimethylsiloxane (Dow Corning 200 Fluid - Dow Corning) | 0.5 g |
| C12/C15 alkyl benzoates (Witconol TN - Witco) | 20 g |
| Triethanolamine | 0.5 g |
| 2,4-Bis{[4-tris(trimethylsiloxy-silylpropyloxy)-2-hydroxy]phenyl}-6-(4-methoxyphenyl)-1,3,5-triazine | 2.5 g |
| Glycerol | 5 g |
| Alkyl hexadecyl phosphate, potassium salt (Amphisol K - Hoffman LaRoche) | 1 g |
| Polyacrylic acid (Synthalen K - 3V) | 0.3 g |
| Hydroxypropylmethylcellulose (Methocel 4FM - Dow Chemical) | 0.1 g |
| 1,4-Bis(benzimidazolyl)phenylene-3,3',5,5'-tetrasulfonic acid | 2 g |
| | 1.5 g |
| Benzene-1,4-bis(3-methylidene-10-camphorsulfonic acid) (Mexoryl SX - Chimex) | 1.5 g |
| Triethanolamine | qs pH 7 |
| Preserving agents | qs |
| Water | 100 g |

EXAMPLE 3

| COMPOSITION | Example 3 |
|---|---|
| 80/20 mixture of cetylstearyl alcohol and of oxyethylenated (33 EO) cetylstearyl alcohol (Sinnowax AO - Henkel) | 7 g |
| Mixture of glyceryl monostearate and distearate (Cerasynt SD-V - ISP) | 2 g |
| Cetyl alcohol | 1.5 g |
| Polydimethylsiloxane (Dow Corning 200 Fluid - Dow Corning) | 1 g |
| C12/C15 alkyl benzoates (Witconol TN - Witco) | 15 g |
| 2,4-bis{[4-(1',1',1',3',5',5',5'-Heptamethyltrisiloxy-2"-methylpropyloxy)-2-hydroxy]phenyl}-6-(4-methoxyphenyl)-1,3,5-triazine | 2 g |
| Glycerol | 15 g |
| 1,4-bis(Benzimidazolyl)phenylene-3,3'5,5'-tetrasulfonic acid | 1.5 g |
| Benzene-1,4-bis(3-methylidene-10-camphorsulfonic acid) (Mexoryl Sx - Chimex) | 2 g |
| Triethanolamine | qs pH 7 |
| Preservatives | qs |
| Demineralized water qs | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition suited for the photoprotection of human skin and/or hair, comprising synergistically UV-photoprotecting effective amounts of each of (a) benzene-1,4-bis(3-methylidene-10-camphorsulfonic acid), optionally in partially or totally neutralized form, (b) at least one bisresorcinyltriazine compound, and (c) at least one compound containing at least two benzoazolyl groups per molecule and/or at least one compound containing at least one benzodiazolyl group per molecule, formulated into a topically applicable, cosmetically acceptable vehicle, diluent or carrier therefor.

2. The sunscreen/cosmetic composition as defined by claim 1, comprising at least one bisresorcinyltriazine compound having the formula (II) below:

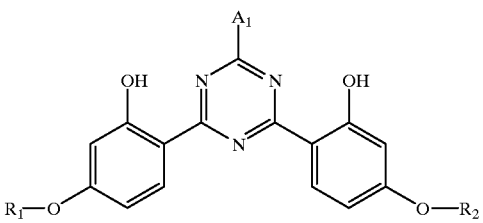

(II)

in which (i) the radicals $R_1$ and $R_2$, which may be identical or different, are each a $C_3$–$C_{18}$ alkyl radical, a $C_2$–$C_{18}$ alkenyl radical, or a residue of formula —$CH_2$—$CH(OH)$—$CH_2$—$OT_1$ in which $T_1$ is a hydrogen atom, or a $C_1$–$C_8$ alkyl radical; or (ii) the radicals $R_1$ and $R_2$, which again may be identical or different, are also each a residue of the formula (1) below:

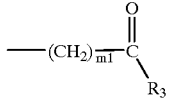

(1)

in which m1 is a number ranging from 1 to 3; $R_3$ is a hydroxyl group, a $C_1$–$C_5$ alkyl radical which is unsubstituted or substituted with one or more hydroxyl groups, a $C_1$–$C_5$ alkoxy radical, an amino group, a mono- or di($C_1$–$C_5$)alkylamino radical, a metal cation M, a residue having one of the formulae (2) to (7) below:

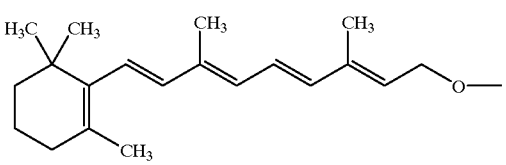

(2)

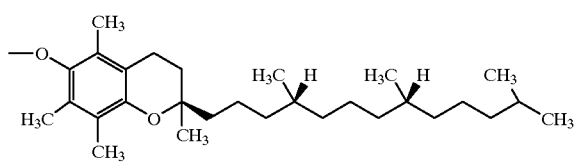

(3)

-continued

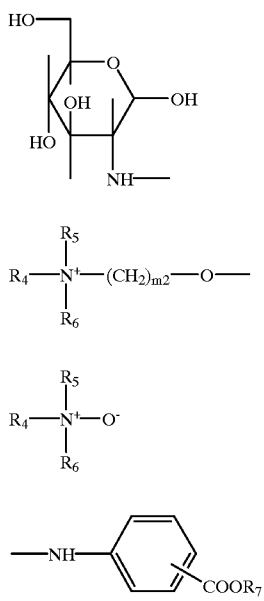
(4)

(5)

(6)

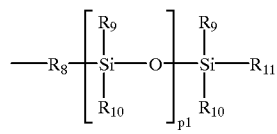
(7)

in which the radicals $R_4$, $R_5$ and $R_6$, which may be identical or different, are each a $C_1$–$C_{14}$ alkyl radical which is unsubstituted or substituted with one or more hydroxyl groups; $R_7$ is a hydrogen atom, a metal cation, a $C_1$–$C_5$ alkyl radical or a residue of formula —$(CH_2)_{m2}$—$OT_1$ in which $m_2$ is a number ranging from 1 to 4 and $T_1$ is as defined above; or (iii) the radicals $R_1$ and $R_2$, which again may be identical or different, are also each a residue of formula (8) below:

(8)

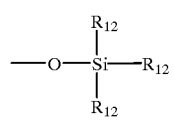

in which $R_8$ is a covalent bond, a linear or branched $C_1$–$C_4$ alkyl radical, or a residue of formula —$C_{m4}H_{2m4}$— or —$C_{m4}H_{2m4}$—O— in which $m_4$ is a number ranging from 1 to 4; $p_1$ is a number ranging from 0 to 5; the radicals $R_9$, $R_{10}$ and $R_{11}$, which may be identical or different, are each a $C_1$–$C_{18}$ alkyl radical, a $C_1$–$C_{18}$ alkoxy radical, or a residue of the formula:

(9)

in which $R_{12}$ is a $C_1$–$C_5$ alkyl radical; $A_1$ is a residue having one of the following formulae:

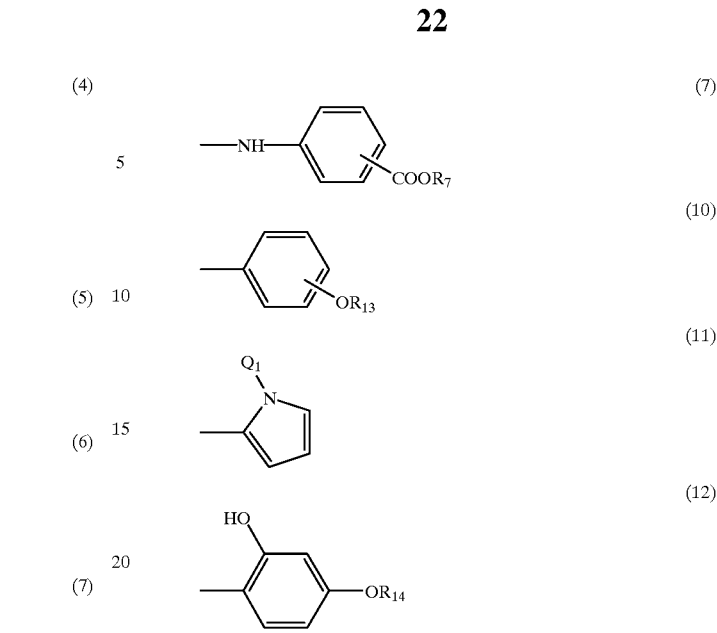
(7)

(10)

(11)

(12)

in which $R_7$ is as defined above: $R_{13}$ is a hydrogen atom, a $C_1$–$C_{10}$ alkyl radical, a radical of formula: —$(CH_2CHR_{16}$—$O)_{n1}R_7$ in which $n_1$ is a number ranging from 1 to 16, $R_{16}$ is a hydrogen atom or methyl, or a residue of structure —$CH_2$—$CH$—$(OH)$—$CH_2OT_1$ wherein $T_1$ is as defined above; $Q_1$ is a $C_1$–$C_{18}$ alkyl radical; $R_{14}$ is a radical having the formula (1):

(1)

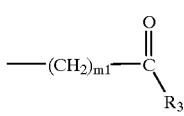

as defined above.

3. The sunscreen/cosmetic composition as defined by claim 2, comprising at least one compound of formula (II) wherein the radical $A_1$ is para-methoxyphenyl or para-ethoxyphenyl and the radicals $R_1$ and $R_2$, which may be identical or different, are each a radical of the structure:

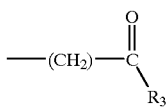

in which $R_3$ is:
   tert-butyloxy;
   OH;
   OM in which M is an alkali metal or alkaline-earth metal cation selected from among a copper, magnesium or zinc cation;
   group of the structure:

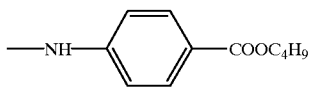

a group of the stucture $O^-N^+(CH_2CH_2OH)_3$;

a group of the structure:

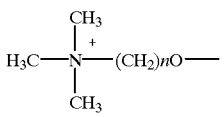

wherein n ranges from 2 to 16;
a group of the structure:

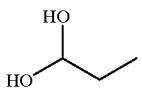

or a group of the structure:

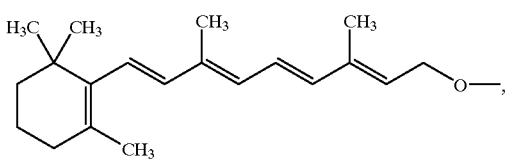

or the radical $A_1$ is para-hydroxyphenyl and the radicals $R_1$ and $R_2$ simultaneously are each a group of the structure:

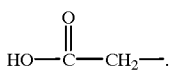

4. The sunscreen/cosmetic composition as defined by claim 2, said at least one compound of formula (II) comprising 2,4-bis{[4-(2-ethylhexyloxy)-2-hydroxy]phenyl}-6-(4-methoxyphenyl)-1,3,5-triazine; 2,4-bis{[4-3-(2-propyloxy)-2-hydroxypropyloxy)-2-hydroxy]phenyl}-6-(4-methoxyphenyl)-1,3,5-triazine; 2,4-bis{[4-(2-ethylhexyloxy)-2-hydroxy]phenyl}-6-[4-(2-methoxyethylcarboxyl)phenylamino]-1,3,5-triazine; 2,4-bis{[4-tris(trimethylsiloxysilylpropyloxy)-2-hydroxy]phenyl}-6-[(4-methoxyphenyl)-1,3,5-triazine; 2,4-bis{[4-(2"-methylpropenyloxy)-2-hydroxy]phenyl}-6-(4-methoxyphenyl)-1,3,5-triazine; 2,4-bis{[4-(1',1',1',3',5',5',5'-heptamethyltrisiloxy-2"-methylpropyloxy)-2-hydroxy]phenyl}-6-(4-methoxyphenyl)-1,3,5-triazine; 2,4-bis{[4-(3-(2-propyloxy)-2-hydroxypropyloxy]-2-hydroxy]phenyl}-6-[(4-ethylcarboxyl)phenylamino]-1,3,5-triazine; or 2,4-bis{[4-(2-ethylhexyloxy)-2-hydroxy]phenyl}-6-(1-methyl-2-pyrrolyl)-1,3,5-triazine.

5. The sunscreen/cosmetic as defined by claim 4, said at least one compound of formula (II) comprising 2,4-bis{[4-(2-ethylhexyloxy)-2-hydroxy]phenyl}-6-(4-methoxyphenyl)-1,3,5-triazine; 2,4-bis{[4-tris(trimethylsiloxysilylpropyloxy)-2-hydroxy]phenyl}-6-(4-methoxyphenyl)-1,3,5-triazine; or 2,4-bis{[4-(1',1',1',3',5',5',5'-heptamethyltrisiloxy-2"-methylpropyloxy)-2-hydroxy]phenyl}-6-(4-methoxyphenyl)-1,3,5-triazine.

6. The sunscreen/cosmetic composition as defined by claim 1, comprising from 0.1% to 15% by weight of said at least one bisresorcinyltriazine compound.

7. The sunscreen/cosmetic composition as defined by claim 6, comprising from 0.2% to 10% by weight of said at least one bisresorcinyltriazine compound.

8. The sunscreen/cosmetic composition as defined by claim 1, said benzene-1,4-bis(3-methylidene-10-camphorsulfonic acid), and/or salt thereof, having the structural formula (I) below:

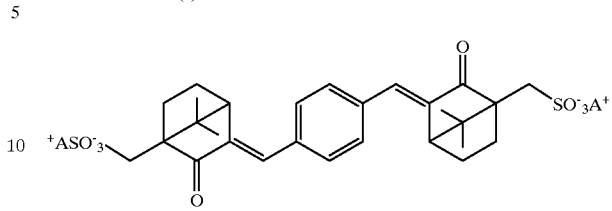

in which A is a hydrogen atom, an alkali metal, or a radical $NH(R)_3^+$ in which the radicals R, which may be identical or different, are each a hydrogen atom, a $C_1$–$C_4$ alkyl or hydroxyalkyl radical, or a group $M^{n+}/n$ wherein $M^{n+}$ is a multivalent metal cation in which n is equal to 2, 3 or 4.

9. The sunscreen/cosmetic composition as defined by claim 1, comprising from 0.1% to 15% by weight of said benzene-1,4-bis(3-methylidene-10-camphorsulfonic acid) or salt thereof.

10. The sunscreen/cosmetic composition as defined by claim 9, comprising from 0.2% to 10% by weight of said benzene-1,4-bis(3-methylidene-10-camphorsulfonic acid) or salt thereof.

11. The sunscreen/cosmetic composition as defined by claim 1, comprising at least one compound containing at least two benzazolyl groups and having the structural formula (III) below:

(III)

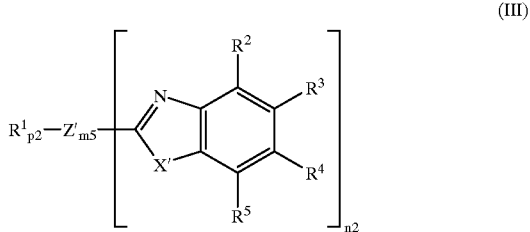

in which Z' is an organic residue of valency ($p_2+n_2$) comprising one or more double bonds located such that it completes the system of double bonds of at least two benzoazolyl groups as defined in the brackets, to form a totally conjugated assembly; X' is S, O or $NR^6$; $R^1$ is a hydrogen atom, $C_1$–$C_{18}$ alkyl radical, a $C_1$–$C_4$ alkoxy radical, a $C_5$–$C_{15}$ aryl radical, a $C_2$–$C_{18}$ acyloxy radical, $SO_3Y''$ or $COOY'$; the radicals $R^2$, $R^3$, $R^4$ and $R^5$, which may be identical or different, are each a nitro group or a radical $R^1$; $R^6$ is a hydrogen atom, a $C_1$–$C_4$ alkyl radical, or a $C_1$–$C_4$ hydroxyalkyl radical; Y' is a hydrogen atom, Li, Na, K, $NH_4$, ½Ca, ½Mg, ⅓Al, or a cation resulting from the neutralization of a free acid group with an organic nitrogenous base; $m_5$ is 0 or 1; $n_2$ is a number ranging from 2 to 6; $p_2$ is a number ranging from 1 to 4; with the proviso that $p_2+n_2$ does not exceed 6.

12. The sunscreen/cosmetic composition as defined by claim 11, wherein formula (III) the radical Z' is (a) a linear olefinic aliphatic $C_2$–$C_6$ hydrocarbon-based radical which may be interrupted with a $C_5$–$C_{12}$ aryl radical or a $C_4$–$C_{10}$ heteroaryl radical; (b) a $C_5$–$C_{15}$ aryl radical which may be interrupted with a linear olefinic aliphatic $C_2$–$C_6$ hydrocarbon-based radical; or (c) a $C_3$–$C_{10}$ heteroaryl radical, with the proviso that the radical Z' may be substituted with $C_1$–$C_6$ alkyl, $C_1$–$C_6$ alkoxy, phenoxy, hydroxyl, methylenedioxy or amino radicals optionally substituted with one or two $C_1$–$C_5$ alkyl radicals.

13. The sunscreen/cosmetic composition as defined by claim 11, wherein formula (III) the radical Z' is selected from among those of the following formulae:

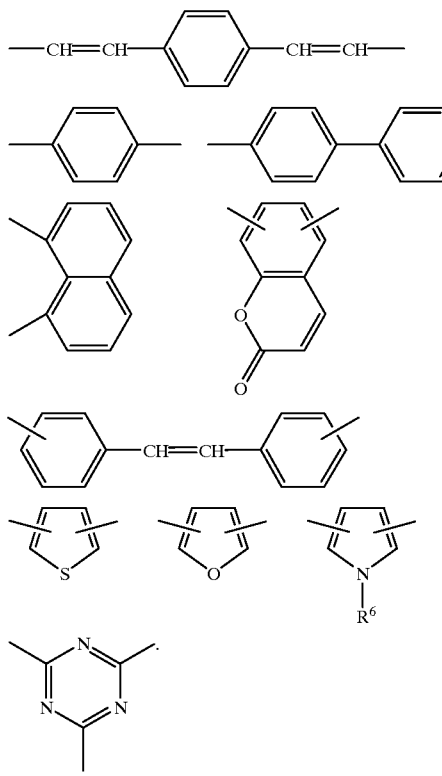

14. The sunscreen/cosmetic composition as defined by claim 11, in which the compound of formula (III) is one of the following, or salt thereof:

Compound 1

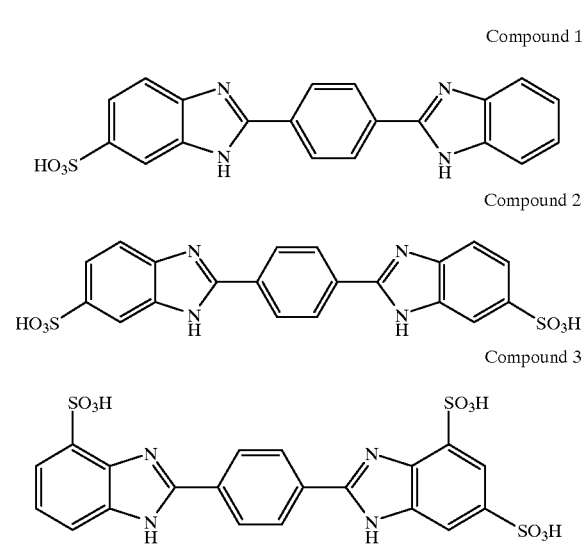

Compound 2

Compound 3

Compound 4

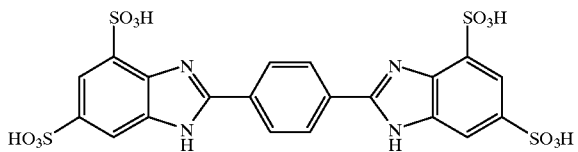

Compound 5

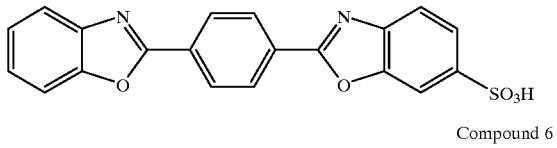

Compound 6

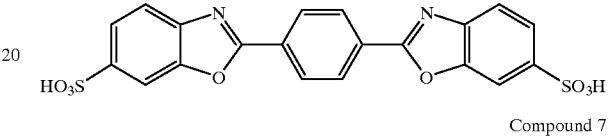

Compound 7

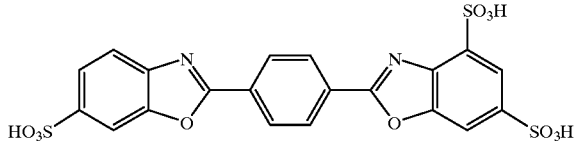

Compound 8

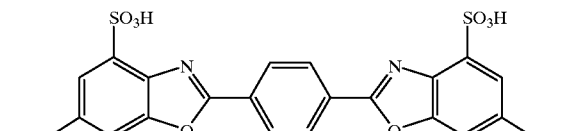

Compound 9

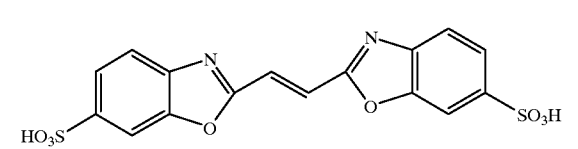

Compound 10

Compound 11

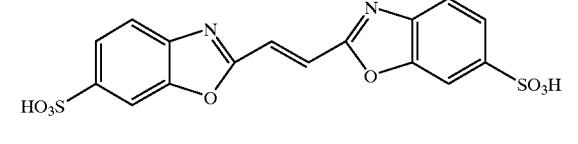

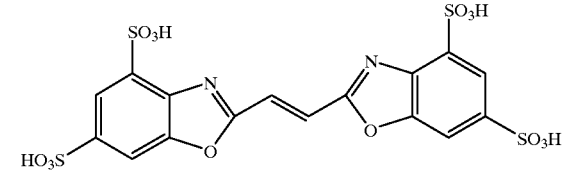

Compound 12
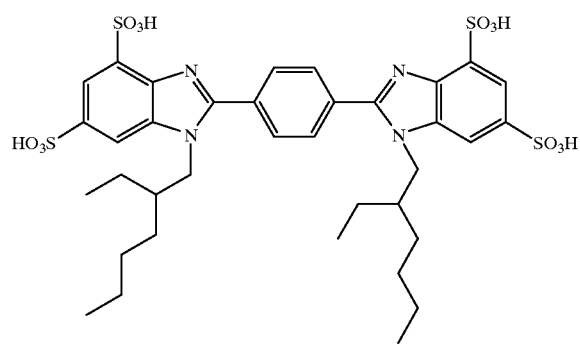
Compound 13
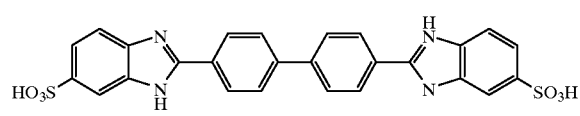
Compound 14
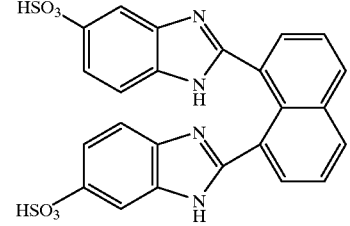
Compound 15
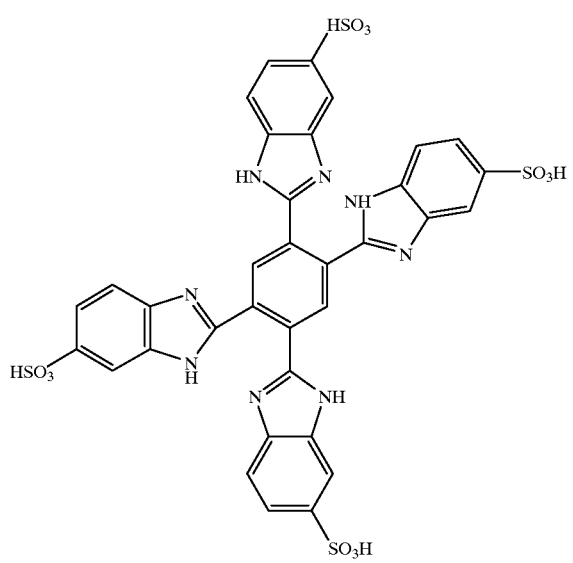
Compound 16
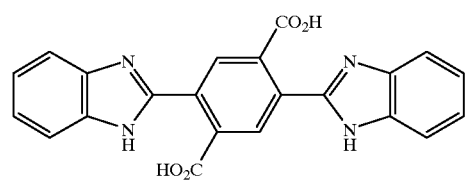
Compound 17
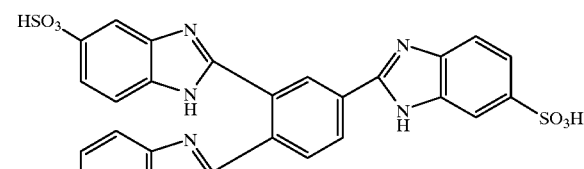
Compound 18
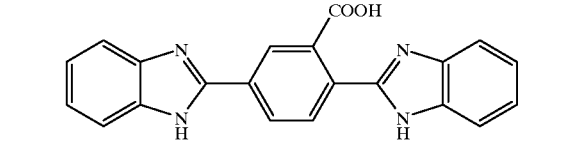
Compound 19
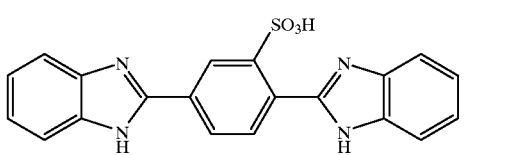
Compound 20
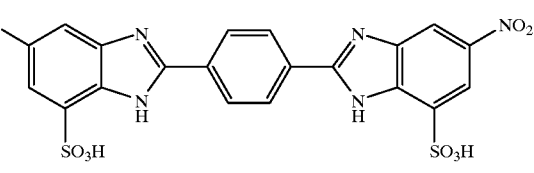
Compound 21
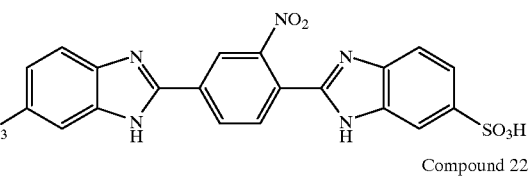
Compound 22
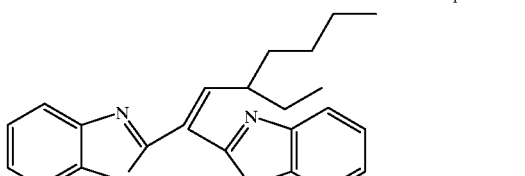
Compound 23
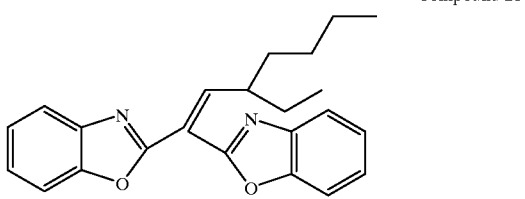
Compound 24
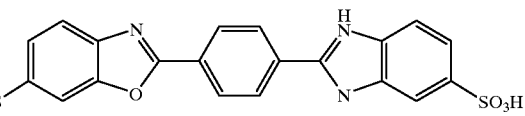

-continued

Compound 25

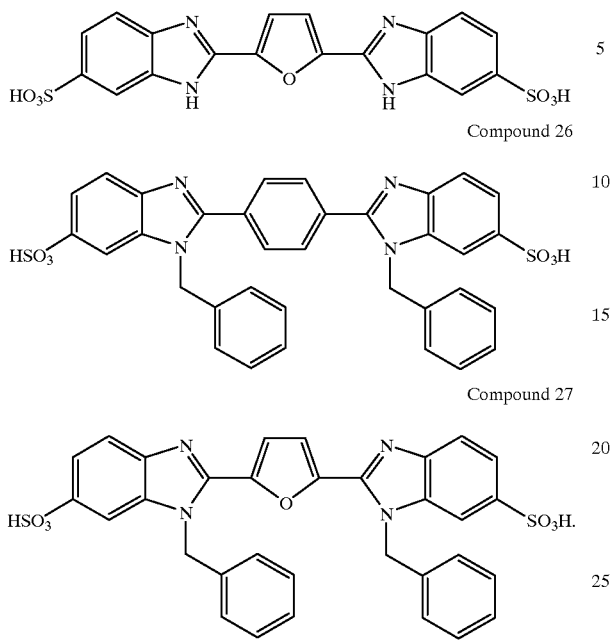

Compound 26

Compound 27

15. The sunscreen/cosmetic composition as defined by claim 11, in which the compound of formula (III) is 1,4-bis(benzimidazolyl)phenylene-3,3',5,5'-tetrasulfonic acid (Compound 4) having the following formula, or salt thereof:

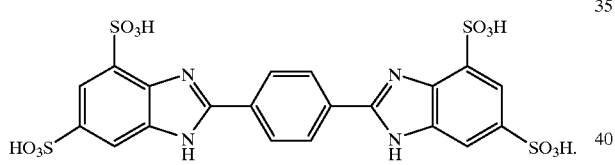

16. The sunscreen/cosmetic composition as defined by claim 11, comprising at least one compound containing at least two benzoazolyl groups and having the following formulae, or salt thereof:

Compound 28

Compound 29

Compound 30

Compound 31

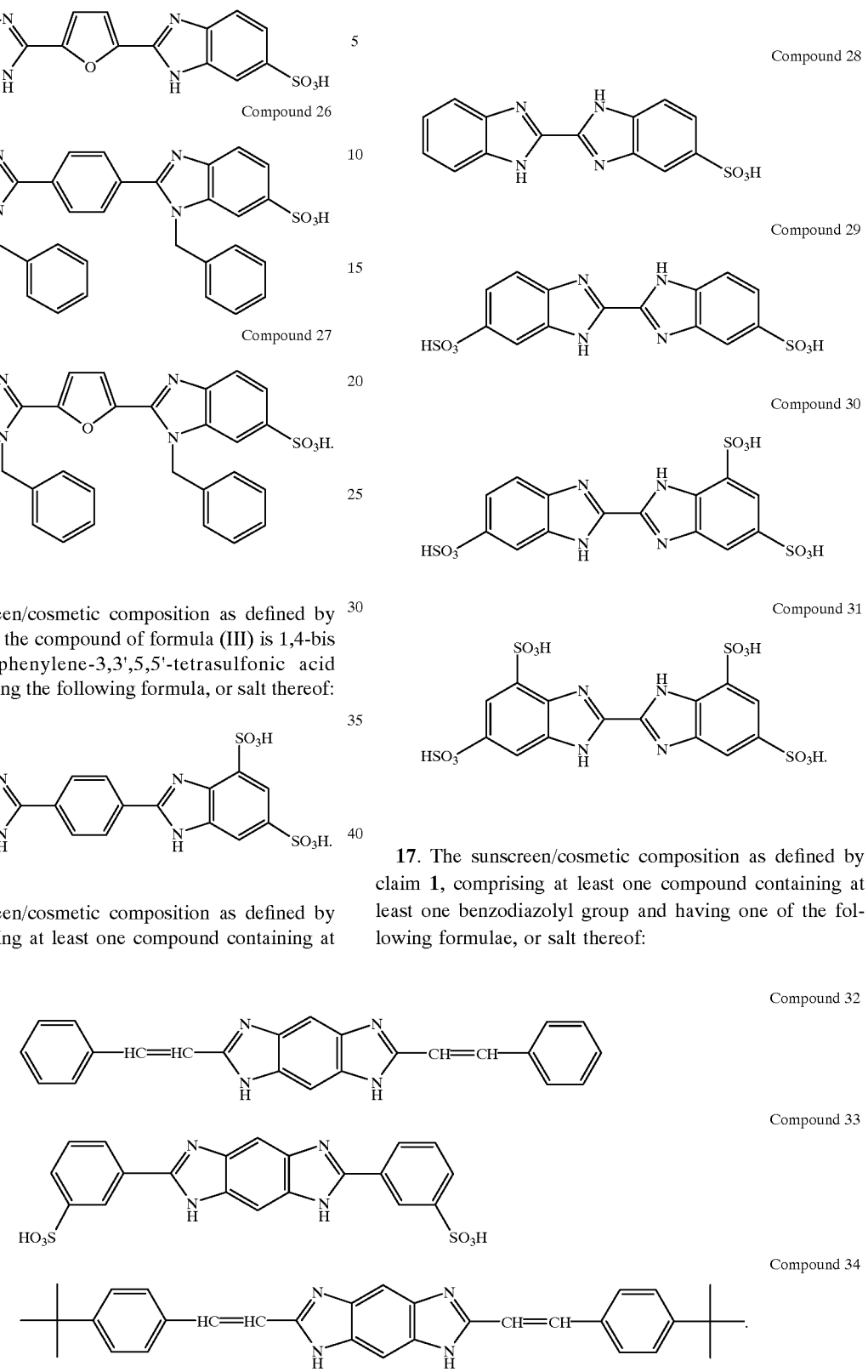

17. The sunscreen/cosmetic composition as defined by claim 1, comprising at least one compound containing at least one benzodiazolyl group and having one of the following formulae, or salt thereof:

Compound 32

Compound 33

Compound 34

18. The sunscreen/cosmetic composition as defined by claim 1, comprising from 0.1% to 15% by weight of said at least one benzoazolyl/benzodiazolyl compound.

19. The sunscreen/cosmetic composition as defined by claim 18, comprising from 0.2% to 10% by weight of said at least one benzoazolyl/benzodiazolyl compound.

20. The sunscreen/cosmetic composition as defined by claim 11 formulated as an oil-in-water is emulsion.

21. The sunscreen/cosmetic composition as defined by claim 1, formulated as a water-in-oil emulsion.

22. The sunscreen/cosmetic composition as defined by claim 1, further comprising at least one additional hydrophilic or lipophilic organic UV-A and/or UV-B sunscreen.

23. The sunscreen/cosmetic composition as defined by claim 22, further comprising at least one cinnamic derivative, salicylic derivative, camphor derivative, triazine derivative, benzophenone derivative, dibenzoylmethane derivative, benzimidazole derivative, β-β-diphenylacrylate derivative, p-aminobenzoic acid derivative, sunscreen polymer, or sunscreen silicone.

24. The sunscreen/cosmetic composition as defined by claim 1, further comprising a photoprotecting effective amount of particulates of at least one coated or uncoated inorganic pigment or nanopigment.

25. The sunscreen/cosmetic composition as defined by claim 14, said at least one pigment or nanopigment comprising titanium dioxide, zinc oxide, iron oxide, zirconium oxide, cerium oxide, or mixture thereof.

26. The sunscreen/cosmetic composition as defined by claim 1, further comprising at least one active agent for the artificial tanning and/or browning of human skin.

27. The sunscreen/cosmetic composition as defined by claim 1, further comprising at least one cosmetically acceptable adjuvant or additive.

28. The sunscreen/cosmetic composition as defined by claim 27, said at least one adjuvant or additive comprising a fat, organic solvent, thickening agent, softener, antioxidant, opacifying agent, stabilizing agent, emollient, hydroxy acid, anti-foaming agent, hydrating agent, vitamin, fragrance, preservative, surfactant, filler, sequestering agent, polymer, propellant, basifying or acidifying agent, dye, colorant, or mixture thereof.

29. The sunscreen/cosmetic composition as defined by claim 1, comprising a nonionic vesicle dispersion, emulsion, cream, milk, gel, cream gel, ointment, suspension, dispersion, powder, solid stick or tube, foam or spray.

30. The sunscreen/cosmetic composition as defined by claim 1, comprising a makeup.

31. The sunscreen/cosmetic composition as defined by claim 30, comprising an anhydrous or aqueous solid or paste, emulsion, suspension, or dispersion.

32. The sunscreen/cosmetic composition as defined by claim 1, comprising a shampoo, lotion, gel, nonionic vesicle dispersion, hair lacquer, or rinse.

33. The sunscreen/cosmetic composition as defined by claim 1, having a sun protection factor of at least 2.

34. A regime/regimen for protecting human skin and/or hair against the deleterious effects of ultraviolet irradiation, comprising topically applying thereto an effective amount of the sunscreen/cosmetic composition as defined by claim 1.

* * * * *